US011147784B2

(12) United States Patent
Rabinowitz et al.

(10) Patent No.: US 11,147,784 B2
(45) Date of Patent: Oct. 19, 2021

(54) DIETARY SUPPLEMENTS AND COMPOSITION FOR TREATING CANCER

(71) Applicants: The Trustees of Princeton University, Princeton, NJ (US); Memorial Sloan-Kettering Cancer Center, New York, NY (US)

(72) Inventors: Joshua D. Rabinowitz, Princeton, NJ (US); Craig B. Thompson, New York, NY (US); Jiangbin Ye, New York, NY (US); Jing Fan, Princeton, NJ (US); Jurre Kamphorst, Princeton, NJ (US)

(73) Assignees: THE TRUSTEES OF PRINCETON UNIVERSITY, Princeton, NJ (US); MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/299,966

(22) Filed: Mar. 12, 2019

(65) Prior Publication Data

US 2019/0209503 A1 Jul. 11, 2019

Related U.S. Application Data

(63) Continuation of application No. 14/901,859, filed as application No. PCT/US2014/045168 on Jul. 1, 2014, now abandoned.

(60) Provisional application No. 61/841,806, filed on Jul. 1, 2013.

(51) Int. Cl.
*A61K 31/198* (2006.01)
*A61K 9/00* (2006.01)
*A61K 45/06* (2006.01)
*A61K 31/7068* (2006.01)
*A61K 31/519* (2006.01)
*A23L 33/175* (2016.01)

(52) U.S. Cl.
CPC .......... *A61K 31/198* (2013.01); *A23L 33/175* (2016.08); *A61K 9/0056* (2013.01); *A61K 31/519* (2013.01); *A61K 31/7068* (2013.01); *A61K 45/06* (2013.01); *A23V 2002/00* (2013.01)

(58) Field of Classification Search
CPC ................ A61K 31/198; A61K 9/0056; A61K 31/7068; A61K 31/519; A61K 45/06; A23L 33/175; A23V 2002/00
USPC .......................................................... 514/43
See application file for complete search history.

(56) References Cited

U.S. PATENT DOCUMENTS

| | | |
|---|---|---|
| 4,499,076 A | 2/1985 | Ohashi et al. |
| 5,514,656 A | 5/1996 | Cope et al. |
| 6,159,506 A | 12/2000 | Bieser et al. |
| 2005/0287204 A1 | 12/2005 | Hageman et al. |
| 2006/0052454 A1 | 3/2006 | Hevia |
| 2007/0269531 A1 | 11/2007 | Wolfe et al. |
| 2010/0113598 A1 | 5/2010 | Cleveland |
| 2011/0129524 A1 | 6/2011 | Imai et al. |
| 2012/0208742 A1 | 8/2012 | Primiano et al. |
| 2013/0020226 A1 | 1/2013 | Abele et al. |
| 2016/0374971 A1 | 12/2016 | Rabinowitz et al. |

FOREIGN PATENT DOCUMENTS

| | | |
|---|---|---|
| DE | 20101225 U1 | 6/2001 |
| WO | WO-98/04255 A1 | 2/1998 |
| WO | WO 2004/000297 | * 12/2003 |

OTHER PUBLICATIONS

Amelio et al., Serine and glycine metabolism in cancer, Trends Biochem. Sci., 39(4):191-8 (2014).
Bradley et al., Non-steroidal anti-inflammatory drugs and pancreatic cancer risk: a nested case-control study, Br. J. Cancer, 102(9):1415-21 (2010).
Cao et al., Methionine-dependence and combination chemotherapy on human gastric cancer cells in vitro, World J. Gastroenterol., 8(2):230-2 (2002).
Fan et al., Quantitative flux analysis reveals folate-dependent NADPH production, Nature, 510(7504):298-302 (2014).
Funahashi et al., Opposing effects of n-6 and n-3 polyunsaturated fatty acids on pancreatic cancer growth, Pancreas, 36(4):353-62 (2008).
Hyndman, Biochemical and functional interactions of methyltetrahydrofolate and homocysteine in vascular disease, A Thesis, Department of Medical Science, University of Calgary, Dec. 15, 2000.
International Preliminary Report on Patentability, International Application No. PCT/US2014/045168, dated Jan. 5, 2016.
International Search Report and Written Opinion, International Application No. PCT/US2014/045168, dated Nov. 17, 2014.
Jain et al., Metabolite profiling identifies a key role for glycine in rapid cancer cell proliferation, Science, 336(6084):1040-4 (2012).
Kamphorst et al., Hypoxic and Ras-transformed cells support growth by scavenging unsaturated fatty acids from lysophospholipids, Proc. Natl. Acad. Sci. USA, 110(22):8882-7 (2013).
Khan et al., HDAC inhibitors in cancer biology: emerging mechanisms and clinical applications, Immunol. Cell Biol., 90(1):85-94 (2012).
Lu et al., Metabolomic analysis via reversed-phase ion-pairing liquid chromatography coupled to a stand alone orbitrap mass spectrometer, Anal. Chem., 82(8):3212-21 (2010).

(Continued)

*Primary Examiner* — Yih-Horng Shiao
(74) *Attorney, Agent, or Firm* — Marshall, Gerstein & Borun LLP

(57) ABSTRACT

Methods and compositions for treating cancer and other disorders associated with undesired cellular proliferation are provided comprising administering to a subject in need thereof an amino acid mixture, wherein the amino acid mixture comprises glycine, optionally comprising at least a 2:1 molar ratio of glycine to serine.

13 Claims, 11 Drawing Sheets

(56) References Cited

OTHER PUBLICATIONS

Maddocks et al., Serine starvation induces stress and p53-dependent metabolic remodelling in cancer cells, Nature, 493(7433):542-6 (2013).
Poirson-Bichat et al., Methionine depletion enhances the antitumoral efficacy of cytotoxic agents in drug-resistant human tumor xenografts, Clin. Cancer Res., 6(2):643-53 (2000).
Snell et al., Enzymic imbalance in serine metabolism in human colon carcinoma and rat sarcoma, Br. J. Cancer, 57(1):87-90 (Jan. 1988).
Williamson, The amino acid composition of human milk proteins, J. Biol. Chem., 156:47-52 (1944).
Zhang et al., Glycine decarboxylase activity drives non-small cell lung cancer tumor-initiating cells and tumorigenesis, Cell, 148(1-2):259-72 (2012).

* cited by examiner

AICAR signal in Δmthfd2 cells

DIETARY SUPPLEMENTS AND COMPOSITION FOR TREATING CANCER

CROSS REFERENCE TO RELATED APPLICATIONS

This application is a U.S. Continuation Application of U.S. patent application Ser. No. 14/901,859, filed Dec. 29, 2015, which is a National Phase Application of International Patent Application No. PCT/US2014/045168, filed Jul. 1, 2014, which claims the priority benefit of U.S. Provisional Patent Application No. 61/841,806, filed Jul. 1, 2013, hereby incorporated by reference.

GOVERNMENT SUPPORT

This invention was made with government support from Grant No. CA163591 awarded by the National Institutes of Health. The government has certain rights in the invention.

FIELD OF THE INVENTION

The invention relates to methods and compositions for treating cancer and other diseases associated with undesired cellular proliferation.

BACKGROUND

There is a rapidly growing recognition of the importance of metabolism to the growth of cancer cells and tumors in mammals. Most of the associated efforts toward development of novel cancer treatments have focused on identifying metabolic enzymes that are selectively important to cancer cells relative to non-transformed or non-growing cells, and then on inhibiting these enzymes using small molecule or macromolecule-based drugs.

A potential alternative approach, although much less explored, to modulating cancer metabolism is via the diet or dietary supplements. Recently it was shown that a low serine diet impairs tumor growth (Maddocks et al., *Nature* 2013 Jan. 24; 493(7433):542-6). The interplay between varying levels of amino acids was not further elucidated, however. Nor was the possibility of combining dietary and pharmacological interventions examined.

Given the complexity of metabolism, which involves 2500 different enzymes and associated chemical reactions in humans, many of which are important in both normal tissues and cancer cells, it is clearly a great challenge to safely and effectively modulate metabolism for the treatment of cancer. However, given that cancer is anticipated to soon be the leading cause of death in developed countries, there is clearly a great need for new methods, compositions, and formulations for its treatment.

SUMMARY

The disclosure is based on the discovery that cellular flux from serine to glycine is necessary to maintain NADPH and thus antioxidant defense and biosynthetic capability, and that if glycine is high while serine is low, flux is in the opposite direction (and/or flux in the forward direction is impaired) and NADPH levels, and to a lesser extent ATP, drop. Thus, by manipulating the ratios of amino acids in cells or the diet, one can control cell growth or susceptibility to oxidative stress, including that induced by chemotherapy or radiation therapy. The following methods and compositions implement this discovery.

In various embodiments of the disclosure, there is provided a nutritional supplement comprising an amino acid mixture, wherein the amino acid mixture comprises at least a 2:1 molar ratio of glycine to serine. In various embodiments, the nutritional supplement is in the form of a powder, a gel, a solution, a suspension, a paste, a solid, a liquid, a liquid concentrate, a reconstitutable powder, a shake, a concentrate, a pill, a bar, a tablet, a capsule or a ready-to-use product.

In some embodiments, the molar ratio of glycine to serine in the supplement is about 3:1, 4:1, 5:1, 6:1, 7:1, 8:1, 9:1, 10:1, 20:1, 30:1, 40:1, 50:1, 60:1, 70:1, 80:1, 90:1, or 100:1.

In some embodiments, the supplement is substantially devoid of serine.

In some embodiments, the amino acid mixture comprises amino acids in free form, in prodrug form, salts, or amino acid esters.

In some embodiments, the nutritional supplement further comprises recombinantly synthesized protein deficient in serine.

In another aspect of the disclosure, there is provided a nutritional supplement comprising an amino acid mixture, wherein the mixture is deficient in methionine.

In some embodiments, the nutritional supplement further comprises homocysteine.

In some embodiments, the nutritional supplement comprises a molar ratio of homocysteine to methionine greater than 1.

In various embodiments of the disclosure, there is provided a method of treating cancer comprising administering to a subject in need thereof a diet comprising a nutritional supplement as described above.

In various embodiments of the disclosure, there is provided a method of treating cancer comprising administering to a subject in need thereof one or more pharmacological inhibitors of cancer cell growth and instructing the subject to consume a diet comprising a nutritional supplement as described above.

In various embodiments of the disclosure, a nutritional supplement high in serine and/or low in glycine, is provided to a subject receiving anti-folate therapy, so as to decrease the side effects of said therapy, and thereby to increase the therapeutic index of the anti-folate treatment. In some embodiments, the molar ratio of serine to glycine is accordingly 3:1, 4:1, 5:1, 6:1, 7:1, 8:1, 9:1, 10:1, 20:1, 30:1, 40:1, 50:1, 60:1, 70:1, 80:1, 90:1, or 100:1. In some embodiments, the supplement comprises high serine wherein the serine is at least 2, 3, 4, 5 or 6 times the average daily intake of serine based on average daily total protein consumption.

In various embodiments, the disclosure provides a nutritional supplement that is high in glycine and low in serine. In some embodiments, the supplement comprises high glycine wherein the glycine is at least 2, 3, 4, 5 or 6 times the average daily intake of glycine based on average daily total protein consumption.

In various embodiments, the disclosure contemplates a pharmaceutical composition comprising glycine in substantial quantities, optionally comprising serine in low serine quantities, and a pharmaceutically acceptable carrier. In various embodiments, the composition (which may be delivered in one or more unit doses per day) comprises high glycine wherein the glycine is at least 2, 3, 4, 5 or 6 times the average daily intake of glycine based on average daily total protein consumption. In various embodiments, the molar ratio of glycine to serine in the composition is about 3:1, 4:1, 5:1, 6:1, 7:1, 8:1, 9:1, 10:1, 20:1, 30:1, 40:1, 50:1, 60:1, 70:1, 80:1, 90:1, or 100:1. In various embodiments, the pharmaceutical composition comprising high glycine is substantially devoid of serine. In various embodiments, the unit dose of glycine is between 250 mg and 25 g, 750 mg and 10 g, 1 g and 5 g, 0.5 g and 5 g, 0.5 g and 2 g, or 1 g and 2 g. In various embodiments, the unit dose of serine is between 250 mg and 25 g, 750 mg and 10 g, 1 g and 5 g, 0.5 g and 5 g, 0.5 g and 2 g, or 1 g and 2 g.

In various embodiments of the disclosure, there is provided a method of depleting cellular NADPH levels in a subject in need thereof comprising administering to a subject in need thereof a diet comprising a nutritional supplement as described above.

In various embodiments of the disclosure, there is provided a method of treating cancer comprising administering to a subject in need thereof one or more pharmacological inhibitors of cancer cell growth and instructing the subject to consume a diet comprising an amino acid mixture, wherein the mixture comprises at least a 2:1 molar ratio of glycine to serine. Exemplary cancers contemplated herein are described in greater detail in the Detailed Description.

In various embodiments, the disclosure provides a method of treating a proliferative disorder comprising a glycine containing composition as described herein. Treatment of the disorder may include modification of diet with glycine containing dietary or nutritional supplements described herein or administration of glycine in another form, and optionally in combination with an anti-folate or another anti-proliferative drug useful for treating a proliferative disorder, such as cancer, pre-cancerous lesions, fibrosis, or autoimmunity. Proliferative disorders include cancer, autoimmune diseases, fibrotic diseases, and other disorders in which alteration of one-carbon transfer is beneficial.

In some embodiments, the diet comprises less than one half the amount of serine or methionine compared to the amount of the recommended average of serine or methionine in the diet.

In some embodiments, the subject is further instructed to consume a diet low in serine, methionine, choline, or a combination thereof.

In some embodiments, the subject is additionally instructed to consume a supplement comprising glycine or homocysteine.

In some embodiments, the pharmacological inhibitor is an inhibitor of folate metabolism. In some embodiments, the inhibitor of folate metabolism is methotrexate or pemetrexed.

In some embodiments, the pharmacological inhibitor is an inhibitor of DNA methylation. In some embodiments, the inhibitor of DNA methylation is azacytidine.

In various embodiments of the disclosure, there is provided a method of treating cancer comprising administering to a subject in need thereof a nutritional supplement, a pharmaceutical composition or a diet comprising at least a 2:1 molar ratio of glycine to serine.

In various embodiments, the disclosure provides a method of treating cancer in a subject comprising administering a chemotherapeutic agent and a pharmaceutical composition or nutritional supplement comprising high glycine, wherein the subject is administered about 4-8 g, 2-8 g, 6-10 g, 4-12 g, 2-12 g, 2-20 g, 4-40 g, or 2-100 g of glycine daily. In some embodiments, the glycine is administered 1, 2, 3 or 4 times daily to achieve the total daily dose of glycine.

Also contemplated is a method of treating cancer in a subject comprising administering a chemotherapeutic agent and a pharmaceutical composition or nutritional supplement comprising high serine levels, wherein the subject is administered about 4-8 g, 2-8 g, 6-10 g, 4-12 g, 2-12 g, 2-20 g, 4-40 g, or 2-100 g of serine daily.

In various embodiments, the chemotherapeutic is an anti-folate.

In some embodiments, the treatment is administered over a time period of at least 2 weeks.

In some embodiments, the treatment is administered over a time period of 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, or until a therapeutic endpoint is observed.

In various embodiments, the nutritional supplement or pharmaceutical composition is administered from one to four times daily, e.g., one, two, three or four times daily.

It is contemplated that the effects of a nutritional supplement herein comprising glycine can be measured in vivo or in vitro using certain biomarkers such as proteins or mRNA for MTHFD1, MTHFD2, SHMT, SHMT2, MTHFD1L, ALDH1L1, ALDH1L2, or small molecule metabolites such as adenine, ATP, ADP, guanine, GTP, GDP, folate, serine, glycine, formyl-THF, methyl-THF, GAR and AICAR. In one embodiment, cellular levels of formyl-THF and methyl-THF levels decrease in the presence of glycine, optionally when serine is absent. In some embodiments, a rise in AICAR with glycine addition is observed. It is contemplated that levels in the biomarkers may be detectable in a sample from a subject receiving treatment and doses of nutritional supplement are adjusted based on the level of biomarker detected. It is further contemplated that patients suitable for treatment with the nutritional supplement may be selected by analysis of the above biomarkers, or by analysis mutations or amplifications in the genome of a cancer, including mutations or amplifications in the above genes.

In various embodiments, the levels of the biomarkers in the subject after receiving a glycine composition herein are altered from wild-type or baseline levels of a control subject or compared to prior to consumption of glycine by the subject by at least 10%, 20%, 30%, 40%, 50%, 75%, 100%, 150%, 200%, 250% 500% or 1000% or any range between these endpoints.

Other features and advantages of the present disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

BRIEF DESCRIPTIONS OF THE DRAWINGS

FIG. 1. Glycine inhibits the growth of cancer cells in the presence of low serine. HEK293T cells were grown in DMEM with the indicated modifications to glycine and serine. "-ser" means DMEM with no serine with normal amount of glycine (0.4 mM).

(FIG. 4B) U13C-serine labels the methyl group that differentiates dTTP from UTP; (FIG. 4C) U13C-glycine does not label the methyl group of dTTP.

Figure 5:
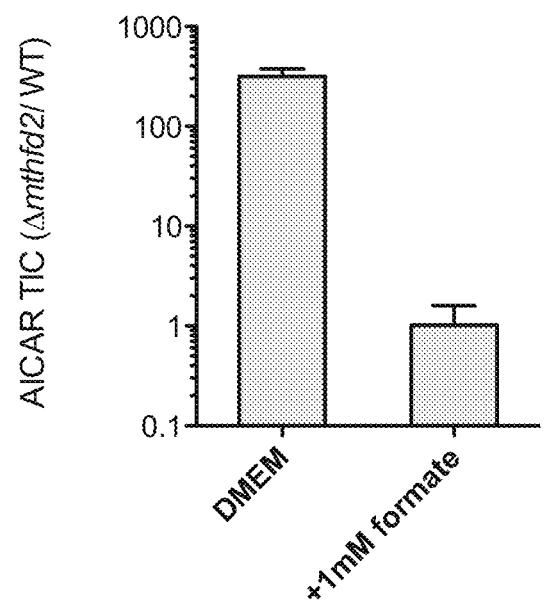

FIG. 5. Addition of formate rectifies the formyl-THF status and thus eliminates the AICAR accumulation in Amthfd2 cells.

Figure 6A:
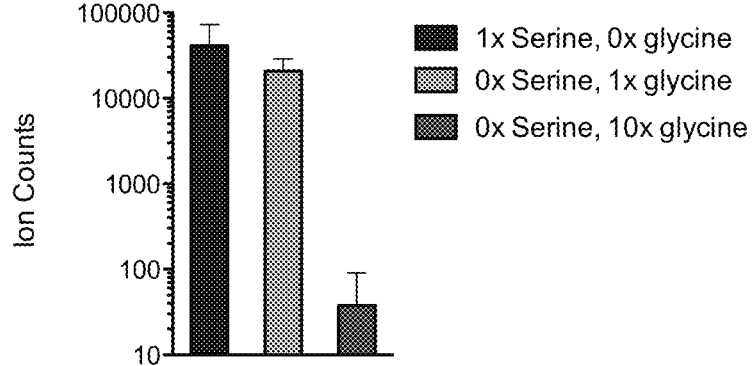
Figure 6B:
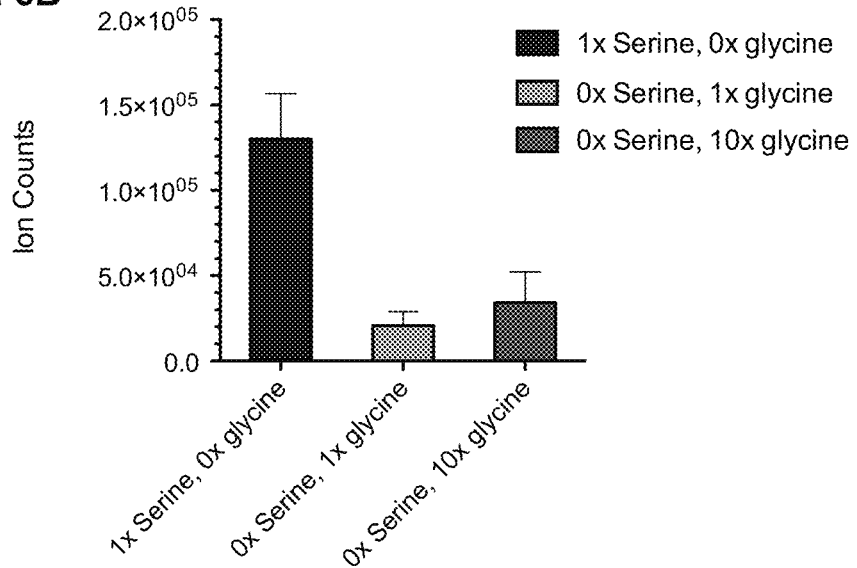
Figure 6C:
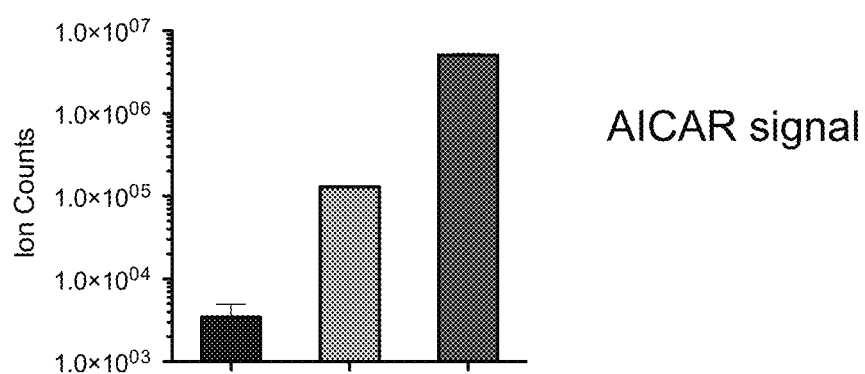

FIGS. 6A-6C show impact of media serine and glycine on formyl-THF (FIG. 6A) and methyl-THF levels; (FIG. 6B) measured in media containing serine and glycine at the levels indicated; (FIG. 6C) AICAR signal increases with folate depletion (culture groups same as in FIG. 6A and FIG. 6B). The concentrations of 1× and 10× are relative to standard DMEM (Dulbecco's Modified Eagle Medium). The Y-axis for the formyl-THF and AICAR is log scale.

Figure 7A:
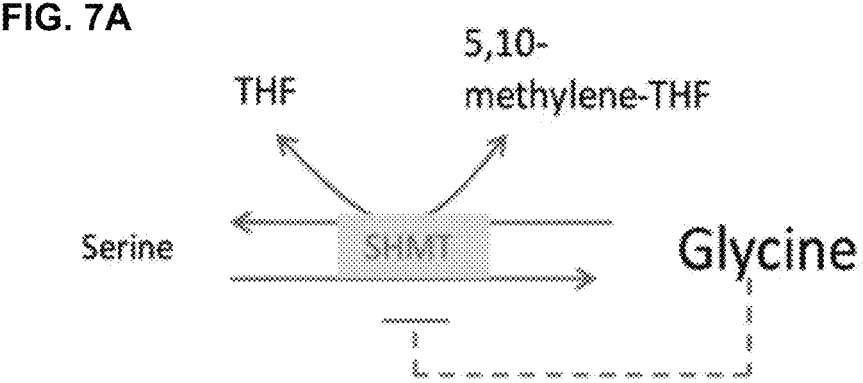
Figure 7B:
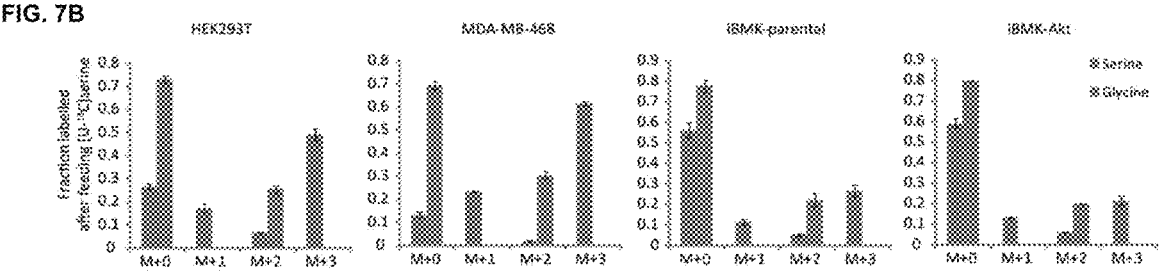
Figure 7C:
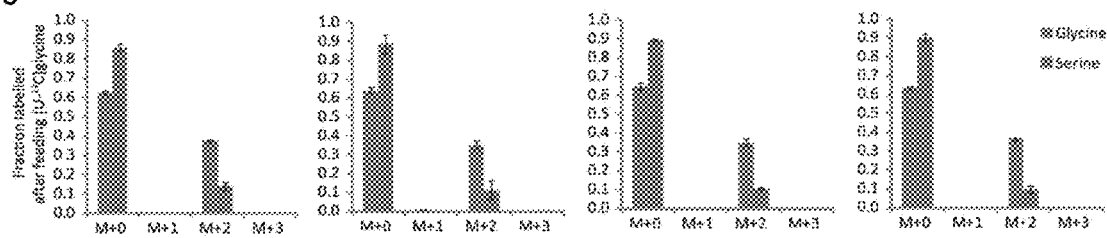

FIGS. 7A-7C show (FIG. 7A) schematic of hydroxymethyltransferase reaction; (FIG. 7B, FIG. 7C) illustration of levels of serine and glycine after feeding with U13C labeled amino acid.

DETAILED DESCRIPTION

The disclosure is based on the discovery that cellular flux from serine to glycine is necessary to maintain NADPH and thus antioxidant defense and biosynthetic capability, and that if glycine is high while serine is low, flux is in the opposite direction (or, minimally, flux in the forward direction is impaired) and NADPH levels, and to a lesser extent ATP, drop. Thus, by manipulating the ratios of amino acids in cells or the diet, one can control cell growth or susceptibility to oxidative stress, including that induced by chemotherapy or radiation therapy.

Thus, one aspect of this invention is providing specific food substitutes or pharmaceutical compositions that can achieve a desired amino acid deficiency for the purpose of treating cancer in a human, in a manner that is tolerable both from a health and taste perspective and is economically viable in terms of cost and availability of ingredients.

Unless otherwise stated, the following terms used in this disclosure, including the specification and claims, have the definitions given below.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1% or 0.05% of a given value or range.

Definition of standard chemistry terms may be found in reference works, including Carey and Sundberg, Advanced Organic Chemistry, 3rd Edition, Vols. A and B (Plenum Press, New York 1992). The practice of the present disclosure employs, unless otherwise indicated, certain conventional methods of synthetic organic chemistry, mass spectrometry, preparative and analytical chromatography, protein chemistry, biochemistry, recombinant DNA technology and pharmacology, within the skill of an ordinary artisan. See, e.g., T. E. Creighton, Proteins: Structures and Molecular Properties (W.H. Freeman and Company, 1993); A. L. Lehninger, Biochemistry (Worth Publishers, Inc., 4th Edition, 2004); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990).

The present disclosure involves partly or completely substituting the normal diet of mammals suffering from cancer, with a prescribed diet containing amino acids such that the molar amount of the amino acids serine, glycine and/or methionine are either 1.5, 2, 3, 4, 5, 7, 10, 15, or 20 times as low as the average abundance of the other amino acids, or 1.5, 2, 3, 4, 5, 7, 10, 15, or 20 times as high. Amino acids in the diet include those in the free form, in peptides or proteins, and in precursor forms including without limitation prodrugs, salts, and amino acid esters. Amino acids with one or more N terminal and/or C terminal modifications are also contemplated, as well as homopolymer forms, including for example and without limitation poly-glycine. Such a diet may potentially be achieved through proper food selection using ingredients available currently off-the-shelf. In such a case, the present disclosure comprises providing the required detailed dietary guidance to achieve the necessary amino acid ratios in the diet. However, such a diet is more readily effectively achieved by replacing some or all of food intake with particularly designed supplements whose compositions are elements of the present disclosure.

The term "nutritional supplement" as used herein refers to a composition comprising one or more amino acids or salts or esters thereof, that is used in a food product, or used or consumed in combination with a food product, to provide a desired level of the amino acid(s) or salt or esters thereof to the subject consuming the supplement. A "dietary supplement" refers to a product taken by mouth that contains a "dietary ingredient" intended to supplement the diet. The dietary ingredients in these products may include: vitamins, minerals, herbs or other botanicals, amino acids, and substances such as enzymes, organ tissues, glandulars, and metabolites.

Nutritional and dietary supplements include such food products in the form of a powder, a gel, a solution, a suspension, a paste, a solid, a liquid, a liquid concentrate, a reconstitutable powder, a shake, a concentrate, a pill, a bar, a tablet, a capsule or a ready-to-use product. It is contemplated that a nutritional or dietary supplement can also be a pharmaceutical composition when the supplement is in the form of a tablet, pill, capsule, liquid, aerosol, injectable solution, or other pharmaceutically acceptable formulation.

The term "high glycine" "high glycine composition" or "high serine" or "high serine composition" refers to a nutritional supplement or pharmaceutical composition that comprises levels of glycine or serine above the normal average protein concentration of glycine or serine, respectively. High glycine refers to a composition comprising 1.5, 2, 3, 4, 5, 6 and up to 10× or 15× or more normal average daily intake by protein consumption. For example, if the total recommended daily average protein intake is approximately 50 g/day, glycine intake could be approximately 7% of this total protein, and therefore average glycine intake would be approximately 3-4 g/day. High glycine is above this average consumption rate. Similarly, high serine refers to a composition comprising 1.5, 2, 3, 4, 5, 6 and up to 10× or 15× or more normal average daily intake by protein consumption. "Low serine" or "low glycine" refers to levels of serine or glycine that are below the average daily intake for that amino acid based on total daily protein intake. Low glycine or low serine includes less than 1× the average intake of the amino acid based on total average protein consumption to substantially devoid of or absence of glycine or serine (or other amino acids or nutrients as indicated), respectively.

The term "therapeutically effective amount" encompasses the amount of a compound or composition that, when administered, is sufficient to prevent development of, or alleviate to some extent, one or more of the symptoms of the condition, disorder or disease being treated. The term "therapeutically effective amount" also encompasses the amount of a compound or composition that is sufficient to elicit the biological or medical response of a cell, tissue, organ, system, animal or human, which is being sought by a researcher, medical doctor or clinician. An appropriate "effective" amount in any individual case may be determined by one of ordinary skill in the art using routine experimentation. It will be understood that the specific dose level and frequency of administration for any particular patient may be varied and will depend upon a variety of factors, including the activity of the specific compound employed; the bioavailability, metabolic stability, rate of excretion and length of action of that compound; the mode and time of administration of the compound; the age, body weight, general health, sex and diet of the patient; and the severity of the particular condition being treated.

The terms "treat", "treating" and "treatment" encompass alleviating or abrogating a condition, disorder or disease, or one or more of the symptoms associated with the condition, disorder or disease, and encompass alleviating or eradicating the cause(s) of the condition, disorder or disease itself. In certain embodiments, the terms "treat", "treating", and "treatment" refer to administration of a compound, a pharmaceutical composition or a pharmaceutical dosage form to a subject for the purpose of alleviating, abrogating or preventing a condition, disorder or disease, or symptom(s) associated therewith, or cause(s) thereof.

The term "pharmaceutical composition" refers to a composition suitable for pharmaceutical use in a subject animal, including humans and mammals. A pharmaceutical composition comprises a therapeutically effective amount of glycine, optionally another biologically active agent, and optionally a pharmaceutically acceptable excipient, carrier or diluent. In certain embodiments, a pharmaceutical composition encompasses a composition comprising the active ingredient(s), and the inert ingredient(s) that make up the excipient, carrier or diluent, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and one or more pharmaceutically acceptable excipient(s), carrier(s) and/or diluent(s).

The term "unit dosage form" refers to physically discrete units suitable as unitary dosages for human and animal subjects, each unit containing a predetermined quantity of an active agent calculated in an amount sufficient to produce the desired effect, optionally in association with a pharmaceutically acceptable excipient, diluent, carrier or vehicle. The specification for a unit dosage form depends on, e.g., the particular active agent and the effect to be achieved, and the pharmacodynamics associated with the active agent in the host.

In certain embodiments, a "pharmaceutically acceptable" substance is suitable for use in contact with cells, tissues or organs of animals or humans without excessive toxicity, irritation, allergic response, immunogenicity or other adverse reactions, in the amount used in the dosage form according to the dosing schedule, and commensurate with a reasonable benefit/risk ratio. In certain embodiments, a "pharmaceutically acceptable" substance that is a component of a pharmaceutical composition is, in addition, compatible with the other ingredient(s) of the composition.

The terms "pharmaceutically acceptable excipient", "pharmaceutically acceptable carrier" and "pharmaceutically acceptable diluent" encompass, without limitation, pharmaceutically acceptable inactive ingredients, materials, compositions and vehicles, such as liquid fillers, solid fillers, diluents, excipients, carriers, solvents and encapsulating materials. Carriers, diluents and excipients also include all pharmaceutically acceptable dispersion media, coatings, buffers, isotonic agents, stabilizers, absorption delaying agents, antimicrobial agents, antibacterial agents, antifungal agents, adjuvants, and so on. Except insofar as any conventional excipient, carrier or diluent is incompatible with the active ingredient, the present disclosure encompasses the use of conventional excipients, carriers and diluents in pharmaceutical compositions. See, e.g., Remington: The Science and Practice of Pharmacy, 21st Ed., Lippincott Williams & Wilkins (Philadelphia, Pa., 2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla., 2004).

A "pharmaceutically acceptable salt" is a salt of a compound that is suitable for pharmaceutical use, including but not limited to metal salts (e.g., sodium, potassium, magnesium, calcium, etc.), acid addition salts (e.g., mineral acids, carboxylic acids, etc.), and base addition salts (e.g., ammonia, organic amines, etc.).

The term "subject" refers to an animal, including but not limited to a mammal, such as a primate (e.g., human or monkey), cow, sheep, goat, pig, horse, dog, cat, rabbit, rat or mouse. The terms "subject" and "patient" are used interchangeably herein in reference, e.g., to a mammalian subject, such as a human subject.

Various embodiments of the present disclosure comprise a food substitute or nutritional supplement, e.g., in the form of a powder or shake. The nutritional supplements contain an imbalance of amino acids generally in the form of a deficiency of one or more amino acids, optionally complemented by a surplus of one or more other amino acids. For example, serine, glycine, and/or methionine are either 1.5, 2, 3, 4, 5, 7, 10, 15, or 20 times as low as the average abundance of the other amino acids, or 1.5, 2, 3, 4, 5, 7, 10, 15, or 20 times as high. In making such an assessment, the abundances of amino acids may optionally be corrected for their average abundance in human protein. The powders, shakes or nutritional supplements typically contain approximately 20-50% of the required daily protein intake with said amino acid deficiencies/overabundances. These powders, shakes or nutritional supplements are to be recommended to be consumed 1-5 or 1-4 times daily, and depending on the specific shake composition, other foods that are low in protein but rich in other nutrients, such as fruits, vegetables and certain nuts can be consumed following a dietician's recommendation, making sure the dietary amino acid intake ratios are kept at the intended ratios. This diet is intended to be consumed alone or in combination with drug therapies such as de-methylation, promethylation, serine pathway inhibition, and/or antifolate therapies.

In various embodiments, a nutritional supplement contains a molar ratio of glycine to serine of about (or greater than) 3:1, 4:1, 5:1, 6:1, 7:1, 8:1, 9:1, 10:1, 20:1, 30:1, 40:1, 50:1, 60:1, 70:1, 80:1, 90:1, or 100:1.

In various embodiments, a nutritional supplement is substantially devoid of serine. As used herein, "substantially devoid" means completely or very nearly free of serine. In various embodiments, the supplement is substantially devoid of serine and contains glycine in excess of the average concentration of other amino acids in the supplement.

For example, without limitation, one embodiment of the present disclosure includes a food substitute in the form of a capsule or a pill, comprising a coating and an interior calorie rich substance, wherein the coating is any pill or capsule coating known in the art and wherein the interior calorie rich substance comprises a molar ratio of glycine to serine of about (or greater than) 3:1, 4:1, 5:1, 6:1, 7:1, 8:1, 9:1, 10:1, 20:1, 30:1, 40:1, 50:1, 60:1, 70:1, 80:1, 90:1, or 100:1. The composition of amino acids is selected to mitigate the growth of cancer in an individual taking the supplement, in comparison to taking an analogous supplement with balanced amino acids.

The nutritional supplement, in various aspects, comprises a total serine content of 0%, 1%, 5%, 10%, 20%, 30%, 40%, 50%, 60%, 70%, 80%, or 90% of the recommended daily intake serine, and approximately 100%, 120%, 150%, 200%, 300%, 500% or 1000% of the recommended daily intake of glycine, or in absolute amounts 2 g, 4 g, 6 g, 8 g, 10 g, 15 g, 20 g, 30 g, 40 g, 50 g, 60 g, or 90 g of glycine.

The disclosed nutritional supplement composition, in various aspects, is provided in any form known in the art, such as a powder, a gel, a solution, a suspension, a paste, a solid, a liquid, a liquid concentrate, a reconstitutable powder, a shake, a concentrate, a pill, a bar, a tablet, a capsule or a ready-to-use product. Moreover, the composition of the present disclosure is, in various embodiments, standardized to a specific caloric content. In various embodiments, the composition is in powder form with a particle size in the range of 5 μm to 1500 μm.

In various embodiments, amino acids are added to the composition in purified, encapsulated and/or chemically or enzymatically-modified form so as to deliver the desired sensory and stability properties. In the case of encapsulation, and in various aspects, the encapsulated amino acids resist dissolution with water but are released upon reaching the small intestine. This result is, in various aspects, achieved by the application of enteric coatings, such as cross-linked alginate and other method well known and routinely practiced in the art.

In various embodiments, the amino acids of the nutritional supplement are provided as intact proteins. In various embodiments, the proteins are provided as a combination of both intact proteins and partially hydrolyzed proteins, with a degree of hydrolysis of between about 4% and 10%. In various embodiments, the proteins are more completely hydrolyzed.

In various embodiments, a nutritional supplement to support the described dietary regimen includes water, sugar, partially hydrolyzed starch from any source/arrowroot/gelatin, cocoa powder (optionally processed with alkali), pea protein or other protein/peptide/amino acid concentrate such that intended amino acids ratios are achieved, and/or canola oil. The supplement may also include less than 0.5% (including optionally zero) of any particular ingredient(s)) of the following: corn oil, magnesium phosphate, cellulose gel, natural and artificial flavor and sweetener, potassium chloride, potassium citrate, calcium carbonate, calcium phosphate, sodium citrate, choline chloride, ascorbic acid, salt, cellulose gum, monoglycerides, soy lecithin, carrageenan, potassium hydroxide, ferric orthophosphate, dl-alpha-tocopheryl acetate, zinc sulfate, niacinamide, manganese sulfate, calcium pantothenate, cupric sulfate, vitamin A palmitate, thiamine chloride hydrochloride, pyridoxine hydrochloride, riboflavin, folic acid, chromium chloride, biotin, sodium molybdate, sodium selenate, potassium iodide, phylloquinone, cyanocobalamin, and vitamin D3, and other vitamins and minerals as follows: vitamin A; vitamin C; calcium; iron; vitamin D; vitamin E; vitamin K; thiamin; riboflavin; niacin; vitamin B6; folate; vitamin B12; biotin; pantothenic acid; phosphorus; iodine; magnesium; zinc; selenium; copper; manganese; chromium; molybdenum; chloride; choline. The above nutritional supplement is advantageously gluten-free; halal; kosher dairy; and suitable for lactose intolerance. It is not suitable for patients with galactosemia. Variants of nutritional supplements (as well as below nutritional supplements) omit selected ingredients such as sugar, folate, choline, canola oil, corn oil, nicotinamide, or any other ingredient as required to achieve the desired therapeutic effect. Such omitted ingredients may optionally be replaced with other related ingredients, e.g., sugar with an artificial sweetener; canola oil and/or corn oil with coconut oil or hydrogenated coconut oil. In certain embodiments, the lipid components of the supplement are selected to be rich in saturated, monounsaturated, omega-3-polyunsaturated, and/or omega-6-polyunsaturated fatty acid. In addition to the protein component, other aspects of the composition may also be selected to mitigate cancer growth. For example, the monoglycerides may be selected to be saturated or to be deficient in omega-6 fatty acids, as omega-6 fatty acids may promote cancer growth, whereas saturated ones may impair cancer growth.

In various embodiments, another exemplary nutritional supplement to support the described dietary regimen includes water, pea protein or other protein/peptides/amino acid concentrate such that intended amino acids ratios are achieved, tricalcium phosphate, dipotassium phosphate, soybean oil, salt, artificial sweeteners, flavors, and color agents, sodium citrate, sucralose, carrageenan, acesulfame potassium.

In various embodiments, another exemplary nutritional supplement to support the described dietary regimen includes water, pea protein or other protein/peptide/amino acid concentrate such that intended amino acids ratios are achieved, sugar, and 2% or less (including optionally zero) of polydextrose, partially hydrolyzed starch from any source/arrowroot/gelatin, canola oil, magnesium phosphate, potassium citrate, gellan gum, calcium phosphate, cellulose gum, natural and artificial flavor and sweetener, soy lecithin, mono- and diglycerides, vitamin C (ascorbic acid), salt, potassium phosphate, carrageenan, vitamin E acetate, corn syrup solids, sucralose, acesulfame, potassium, biotin, vitamin A palmitate, niacinamide, ferric pyrophosphate, calcium pantothenate, zinc sulfate, vitamin D3, manganese sulfate, vitamin K1, vitamin B6 (pyridoxine hydrochloride), vitamin B1 (thiamin hydrochloride), Red3 or other coloring agent, vitamin B2 (riboflavin), potassium iodide, vitamin B12, folic acid, yellow 6 or other coloring agent, chromium chloride, blue 1, sodium molybdate, sodium selenite, sweetened with nutritive and nonnutritive sweeteners and additional vitamins and minerals: vitamin A; vitamin C; calcium; iron; vitamin D; vitamin E; vitamin K; thiamin; riboflavin; niacin; vitamin B6; folate; vitamin B12; biotin; pantothenic acid; phosphorus; iodine; magnesium; zinc; selenium; copper; manganese; chromium; molybdenum; chloride; choline.

In various embodiments, another exemplary nutritional supplement to support the described dietary regimen includes pea protein or other protein/peptide/amino acid concentrate such that intended amino acids ratios are achieved, partially hydrolyzed starch from any source, arrowroot/gelatin, cocoa (optionally processed with alkali), sunflower oil, crystalline fructose, medium chain triglycerides, microcrystalline cellulose, natural and artificial flavor, soy lecithin, potassium citrate, magnesium phosphate, sodium hexametaphosphate, potassium chloride, sucralose, sodium chloride, carrageenan gum, xanthan gum, and acesulfame potassium.

In various embodiments, another exemplary nutritional supplement to support the described dietary regimen includes water, protein/peptide/amino acid mixture as prescribed above, sunflower oil, canola oil, alkalized cocoa powder, partially hydrolyzed starch from any source including from arrowroot/gelatin, crystalline fructose, potassium citrate, whey protein concentrate, natural & artificial flavors, cellulose gum, cellulose gel, soy lecithin, magnesium phosphate, medium chain triglycerides, monosodium phosphate, sodium hexametaphosphate, potassium chloride, acesulfame potassium, carrageenan, tricalcium phosphate, ascorbic acid, salt, ferric pyrophosphate, dicalcium phosphate, sucralose, vitamin E acetate, D calcium pantothenate, niacinamide, zinc oxide, copper gluconate, vitamin A palmitate, pyridoxine HCL, thiamine mononitrate, riboflavin, chromium chloride, folic acid, biotin, potassium iodide, cholecalciferol, and cyanocobalamin.

The amino acid source in the above nutritional supplements can be selected from any appropriate naturally occurring, engineered, or synthesized source, including from beans, peas, or rice, natural or engineered to be deficient or rich in the amino acids serine, glycine, and/or methionine.

Cancers and Proliferative Disorders

It is contemplated that the dietary or nutritional supplements, pharmaceutical composition and other treatment regimens described herein are useful to treat cancers and reduce cancer cell growth. Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In some embodiments, the cancer is selected from the group consisting of breast cancer, liver cancer, colon cancer, lung cancer and prostate cancer.

It is further provided that glycine containing compositions are useful to treat diseases or disorders in which aberrant or otherwise undesired proliferation of cells can lead to a debilitating disorder. It is contemplated that glycine has anti-proliferative effects in these disorders, similar to the effects of antifolates and/or additive or synergistic with the effects of anti-folates. It is also contemplated that a glycine composition of the present disclosure is useful to treat a disease or disorder in which alteration of one-carbon transfer is beneficial.

Such diseases or disorders include, but are not limited to, autoimmune diseases, rheumatoid arthritis, multiple sclerosis, endocrine opthalmopathy, uveoretinitis, systemic lupus erythematosus, myasthenia gravis, Grave's disease, glomerulonephritis, autoimmune hepatological disorder, inflammatory bowel disease (e.g., Crohn's disease or ulcerative colitis), anaphylaxis, allergic reaction, Sjogren's syndrome, type I diabetes mellitus, primary biliary cirrhosis, Wegener's granulomatosis, fibromyalgia, polymyositis, dermatomyositis, inflammatory myositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease (also known as Kawasaki syndrome or Mucocutaneous Lymph Node Syndrome), dengue, encephalomyelitis, endocarditis, endomyocardial fibrosis, endophthalmitis, erythema elevatum et diutinum, psoriasis, psoriatic arthritis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, acute respiratory distress syndrome, pulmonary inflammation, osteoporosis, delayed type hypersensitivity and autoimmune gonadal failure), fibrotic diseases, such as scarring, chronic fibrosis, or pulmonary fibrosis, scleroderma, and fibromyalgia.

Pharmaceutical Compositions

In additional embodiments, the disclosure provides pharmaceutical compositions comprising glycine (or serine) composition, including salts or esters thereof, and one or more pharmaceutically acceptable excipients, carriers and/or diluents. In certain embodiments, the compositions further comprise one or more other biologically active agents as described herein (e.g., antitumor agents, anticancer agents, apoptosis-inducing agents, antioxidants, antifolates, etc.).

In some embodiments, the compositions comprise the desired glycine (or serine) composition in at least about 70%, 75%, 80%, 85%, 90%, 95%, 96%, 97%, 98% or 99% purity.

Non-limiting examples of excipients, carriers and diluents include vehicles, liquids, buffers, isotonicity agents, additives, stabilizers, preservatives, solubilizers, surfactants, emulsifiers, wetting agents, adjuvants, and so on. The compositions can contain liquids (e.g., water, ethanol); diluents of various buffer content (e.g., Tris-HCl, phosphate, acetate buffers, citrate buffers), pH and ionic strength; detergents and solubilizing agents (e.g., Polysorbate 20, Polysorbate 80); anti-oxidants (e.g., methionine, ascorbic acid, sodium metabisulfite); preservatives (e.g., Thimerosol, benzyl alcohol, m-cresol); and bulking substances (e.g., lactose, mannitol, sucrose). The use of excipients, diluents and carriers in the formulation of pharmaceutical compositions is known in the art; see, e.g., Remington's Pharmaceutical Sciences, 18$^{th}$ Edition, pages 1435-1712, Mack Publishing Co. (Easton, Pa. (1990)), which is incorporated herein by reference in its entirety.

For example, carriers include without limitation diluents, vehicles and adjuvants, as well as implant carriers, and inert, non-toxic solid or liquid fillers and encapsulating materials that do not react with the active ingredient(s). Non-limiting examples of carriers include phosphate buffered saline, physiological saline, water, and emulsions (e.g., oil/water emulsions). A carrier can be a solvent or dispersing medium containing, e.g., ethanol, a polyol (e.g., glycerol, propylene glycol, liquid polyethylene glycol, and the like), a vegetable oil, and mixtures thereof.

In some embodiments, the compositions are liquid formulations. In certain embodiments, the formulations comprise a glycine composition in a concentration range from about 0.1 mg/mL to about 20 mg/mL, or from about 0.5 mg/mL to about 20 mg/mL, or from about 1 mg/mL to about 20 mg/mL, or from about 0.1 mg/mL to about 10 mg/mL, or from about 0.5 mg/mL to about 10 mg/mL, or from about 1 mg/mL to about 10 mg/mL.

In further embodiments, the compositions comprise a buffer solution or buffering agent to maintain the pH of the glycine solution or suspension within a desired range. Non-limiting examples of buffer solutions include phosphate buffered saline, Tris buffered saline, and Hank's buffered saline. Buffering agents include without limitation sodium acetate, sodium phosphate, and sodium citrate. Mixtures of buffering agents can also be used. In certain embodiments, the buffering agent is acetic acid/acetate or citric acid/citrate. The amount of buffering agent suitable in a composition depends in part on the particular buffer used and the desired pH of the solution or suspension. For example, acetate is a more efficient pH buffer at pH 5 than pH 6, so less acetate may be used in a solution at pH 5 than at pH 6. In some embodiments, the buffering agent has a concentration of about 10 mM±5 mM. In certain embodiments, the pH of a composition is from about pH 3 to about pH 7.5, or from about pH 3.5 to about pH 7, or from about pH 3.5 to about pH 6.5, or from about pH 4 to about pH 6, or from about pH 4 to about pH 5, or is at about pH 5.0±1.0.

In other embodiments, the compositions contain an isotonicity-adjusting agent to render the solution or suspension isotonic and more compatible for injection. Non-limiting examples of isotonicity agents include NaCl, dextrose, glucose, glycerin, sorbitol, xylitol, and ethanol. In certain embodiments, the isotonicity agent is NaCl. In certain embodiments, NaCl is in a concentration of about 160±20 mM, or about 140 mM±20 mM, or about 120±20 mM, or about 100 mM±20 mM, or about 80 mM±20 mM, or about 60 mM±20 mM.

In yet other embodiments, the compositions comprise a preservative. Preservatives include, but are not limited to, m-cresol and benzyl alcohol. In certain embodiments, the preservative is in a concentration of about 0.4%±0.2%, or about 1%±0.5%, or about 1.5%±0.5%, or about 2.0%±0.5%.

In still other embodiments, the compositions contain an anti-adsorbent. Anti-adsorbents include without limitation benzyl alcohol, Polysorbate 20, and Polysorbate 80. In certain embodiments, the anti-adsorbent is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%.

In additional embodiments, the compositions comprise a stabilizer. Non-limiting examples of stabilizers include glycerin, glycerol, thioglycerol, methionine, and ascorbic acid and salts thereof. In some embodiments, when the stabilizer is thioglycerol or ascorbic acid or a salt thereof, the stabilizer is in a concentration from about 0.1% to about 1%. In other embodiments, when the stabilizer is methionine, the stabilizer is in a concentration from about 0.01% to about 0.5%, or from about 0.01% to about 0.2%. In still other embodiments, when the stabilizer is glycerin, the stabilizer is in a concentration from about 5% to about 100% (neat).

In further embodiments, the compositions contain an antioxidant. Exemplary anti-oxidants include without limitation methionine and ascorbic acid. In certain embodiments, the molar ratio of antioxidant to glycine compound is from about 0.1:1 to about 15:1, or from about 0.5:1 to about 10:1, or from about 1:1 to about 10:1 or from about 3:1 to about 10:1.

Pharmaceutically acceptable salts can be used in the compositions, including without limitation mineral acid salts (e.g., hydrochloride, hydrobromide, phosphate, sulfate), salts of organic acids (e.g., acetate, propionate, malonate, benzoate, mesylate, tosylate), and salts of amines (e.g., isopropylamine, trimethylamine, dicyclohexylamine, diethanolamine). A thorough discussion of pharmaceutically acceptable salts is found in *Remington's Pharmaceutical Sciences*, 18$^{th}$ Edition, Mack Publishing Company, (Easton, Pa. (1990)).

The pharmaceutical compositions can be administered in various forms, such as tablets, capsules, granules, powders, solutions, suspensions, emulsions, ointments, and transdermal patches. The dosage forms of the compositions can be tailored to the desired mode of administration of the compositions. For oral administration, the compositions can take the form of, e.g., a powder, tablet or capsule (including softgel capsule), or can be, e.g., an aqueous or nonaqueous solution, suspension or syrup. Tablets and capsules for oral administration can include one or more commonly used excipients, diluents and carriers, such as mannitol, lactose, glucose, sucrose, starch, corn starch, sodium saccharin, talc, cellulose, magnesium carbonate, and lubricating agents (e.g., magnesium stearate, sodium stearyl fumarate). If desired, flavoring, coloring and/or sweetening agents can be added to the solid and liquid formulations. Other optional ingredients for oral formulations include without limitation preservatives, suspending agents, and thickening agents. Methods of preparing solid and liquid dosage forms are known, or will be apparent, to those skilled in this art (see, e.g., Remington's Pharmaceutical Sciences, referenced above).

Formulations for parenteral administration can be prepared, e.g., as liquid solutions or suspensions, as solid forms suitable for solubilization or suspension in a liquid medium prior to injection, or as emulsions. For example, sterile injectable solutions and suspensions can be formulated according to techniques known in the art using suitable diluents, carriers, solvents (e.g., buffered aqueous solution, Ringer's solution, isotonic sodium chloride solution), dispersing agents, wetting agents, emulsifying agents, suspending agents, and the like. In addition, sterile fixed oils, fatty esters, polyols and/or other inactive ingredients can be used. As further examples, formulations for parenteral administration include aqueous sterile injectable solutions, which can contain antioxidants, buffers, bacteriostats, and solutes that render the formulation isotonic with the blood of the intended recipient; and aqueous and nonaqueous sterile suspensions, which can contain suspending agents and thickening agents.

In addition, pharmaceutical compositions comprising a glycine composition described herein can be formulated as a slow release, controlled release or sustained release system for maintaining a relatively constant level of dosage over a desired time period, such as 1 day, 2 days, 5 days, 1 week or 2 weeks or more. Slow release, controlled release and sustained release formulations can be prepared using, e.g., biodegradable polymeric systems (which can comprise, e.g., hydrophilic polymers), and can take the form of, e.g., microparticles, microspheres or liposomes, as is known in the art.

In some embodiments, the glycine or serine compositions described herein are administered such that the daily dose of glycine or serine is 1.5, 2, 3, 4, 5, 6 and up to 10× to 15× normal average daily intake by protein consumption. In various embodiments, the daily intake of glycine is from 4 to 30 g, from 6 to 16 g, from 10 to 14 g, from 6 to 10 g, from 4 to 12 g or from 4 to 8 g, 2 to 8 g, 2 to 12 g, 2 to 20 g, 4 to 40 g, or 2 to 100 g/day. It is contemplated that the glycine composition is administered in the form of a dietary supplement, such as a shake or bar, and/or as a pharmaceutical composition. For example, if the total recommended daily average protein intake is 50 g/day, glycine intake could be approximately 7% of this total protein, and therefore would be approximately 3-4 g/day.

In various embodiments, the daily intake of serine is from 4 to 30 g, from 6 to 16 g, from 10 to 14 g, from 6 to 10 g, from 4 to 12 g, from 4 to 8 g, 2 to 8 g, 2 to 12 g, 2 to 20 g, 4 to 40 g, or 2 to 100 g/day. It is contemplated that the serine composition is administered in the form of a dietary supplement, such as a shake or bar, and/or as a pharmaceutical composition.

Combinations of Glycine and Chemotherapeutic Interventions

Various amino acids, for example and without limitation, methionine, serine, glycine, and other nutrient components such as, and without limitation, choline, play a role in the methionine cycle, which is important in methylation of DNA, proteins, and lipids. Interfering with this metabolic pathway by modulating amino acid and choline levels affects tumor growth and synergizes with chemotherapeutic agents that work by a variety of mechanisms. Potential synergistic affects exist with azacitidine and other DNA and RNA hypomethylating agents (such as decitabine). Hypomethylation, through inhibition of methyltransferases by azacitidine and comparable agents, impairs DNA synthesis and alters tumor growth by modulating RNA expression. This effect is potentiated by reducing dietary levels of methionine, serine, and/or choline and/or increasing levels of glycine. This result leads to reduced synthesis of compounds important for tumor growth, including both NADPH and S-adenosyl-methionine (SAM). Lower SAM and/or higher homocysteine or SAH results in reduced methylation potential, altered gene transcription, and impaired cancer growth. Conversely, promethylation therapies with histone deacetylase (HDAC) inhibitors, such as vorinostat and romidepsin have shown promise in hematological malignancies, such as cutaneous T-cell lymphoma (Khan et al, Immunol Cell Biol, 2012) and their utility may extend to other types of cancer as well. The potency of such therapies would benefit from modulated diets high in methionine, serine, and choline, and low or high in glycine. Another class of drugs that may synergize with diet are the antifolates such as methotrexate and pemetrexed. These compounds inhibit dihydrofolate reductase (DHFR), potentially in addition to other folate enzymes, leading to reduced synthesis of DNA purine and pyrimidine precursors as well as a reduced donation of methyl groups to the methionine cycle (by 5-methyl-tetrahydrofolate (THF)). Surprisingly, we have recently discovered that one of the fastest and strongest cellular effects of anti-folate therapy (specifically methotrexate, 500 nM) is to decrease the NADPH/NADP+ ratio. This surprising response can be understood in light of our recent discovery that folate-mediated flux from serine towards purines or from serine towards $CO_2$ is a major cellular route of reducing NADP+ to NADPH. Thus, an important novel mechanism of action of anti-folates is to prevent serine-mediated NADPH production, and dietary manipulations (or other forms of supplementation) that decrease serine or increase glycine will synergistically enhance this effect. Antifolates are being used for the treatment of breast, head and neck cancers, leukemia, lymphoma, lung, osteosarcoma, bladder and trophoblastic neoplasms, as well as pleural mesothelioma, and their usefulness would extend to other types of cancers and other diseases such as autoimmune diseases and ectopic pregnancy. As antifolate therapy reduces entry of carbon from serine to the methionine cycle, the effect may also be potentiated by reducing methionine and/or choline levels, or by increasing them. Thus, in some embodiments, the present disclosure includes compositions for treating cancer that combine an anti-folate with glycine, or combine an anti-folate with a serine-deficient and/or glycine-excess protein source (such as an appropriately designed protein shake). In other embodiments, the present disclosure includes methods for treating cancer comprising administration of a therapeutically effective dose of an anti-folate in combination with dietary, dietary supplement, or pharmacological interventions that enhance glycine or deplete serine from the tumor.

Combination of Glycine Supplements with Drug Therapy in Mammals with Cancer

The powders, shakes, and nutritional supplements and other dietary guidance described above are, in various embodiments, used on their own to slow tumor growth for a variety of cancer types. In addition, they are, in various embodiments, used in combination with various kinds of chemotherapeutic agents.

Diets low in methionine, serine and high in glycine potentiate the effects on cancer cells of chemotherapy and/or radiotherapy. Without being bound by theory, this could partly be explained by a reduced ability to produce energy in the form of ATP, reducing power in the form of NADPH, or methylation potential in the form of SAM. Methionine can be metabolized to S-adenosyl methionine (SAM), the key donor in many methylation reactions. The metabolism of serine to glycine leads to the production of NADPH via oxidation of methylene-THF or formyl-THF. NADPH in turn has the ability to reduce oxidized glutathione, thereby aiding cellular capacity to mitigate the effects of reactive oxygen species (ROS). Proper defense against ROS is critical to normal mitochondrial function, and in turn to maintenance of ATP levels. Of note, glycine and cysteine are both precursors for glutathione synthesis and thus may also contribute to maintaining redox balance. Therefore, by modulating the levels in the diet of the amino acids methionine, serine, glycine, and/or cysteine, cellular energy and redox potential is compromised and this synergizes with chemotherapy or radiotherapy due to the increased energy needs, methylation needs, homeostatic challenges and ROS production induced by these therapies. For solid tumors, the modulated diets are combined with radiation therapy. For both solid tumors and hematological malignancies, the modulated diets are combined with any chemotherapy agent known in the art, e.g., with cisplatin or an alternative platinum agent, doxorubicin, carmustine, methotrexate, pemetrexed, 5-fluorouracil, gemcitabine, azacitidine, or with any kinase inhibitor, hormone receptor modulator, or anti-cancer antibody known in the art, as further described below.

In various embodiments, the disclosed nutritional supplements are administered to a cancer patient during a chemotherapeutic regimen. The chemotherapeutic regimen can comprise administration of any chemotherapeutic agent known in the art. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine;

dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above.

In various embodiments, the diet is administered over a time period of at least 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, or until a therapeutic endpoint is observed, e.g., tumor shrinkage is observed.

In various embodiments, the nutritional supplement is administered from one to four times daily, e.g., one, two, three or four times daily.

In various embodiments, the diet comprises less than one quarter or one half the amount of serine or methionine compared to the amount of the recommended average of serine or methionine in the diet. "Recommended average" is defined as the daily intake level of a nutrient that is considered to be sufficient to meet the requirements of 97-98% of healthy individuals.

It is contemplated that the effects of a nutritional supplement herein comprising glycine, or any combination therapy comprising the nutritional supplement, is measured in vivo or in vitro using certain biomarkers such as formyl-THF, methyl-THF and AICAR. In one embodiment, cellular levels of formyl-THF and methyl-THF levels decrease in the presence of glycine, optionally when serine is absent. In some embodiments, a rise in AICAR with glycine addition is observed. It is contemplated that levels in the biomarkers may be detectable in a sample from a subject receiving treatment and doses of nutritional supplement are adjusted based on the level of biomarker detected.

Methods for measuring the biomarkers are described herein and techniques are known in the art.

While the disclosure has been described in conjunction with specific embodiments thereof, the foregoing description as well as the examples which follow are intended to illustrate and not limit the scope of the disclosure. Other aspects, advantages and modifications within the scope of the disclosure will be apparent to those skilled in the art.

EXAMPLES

The following examples are provided for illustration and are not in any way to limit the scope of the invention.

Example 1

Glycine Inhibits the Growth of Cancer Cells in the Presence of Low Serine.

To determine the effect of serine and glycine concentrations on transformed cell growth, HEK293T cells (acquired from ATCC) were cultured in 6 medium conditions: (i) Dulbecco's modified eagle media (DMEM) supplemented with 10% fetal bovine serum (0.4 mM glycine and 0.4 mM serine) ("Standard medium"), (ii) standard medium with addition of 2 mM glycine, (iii) standard medium with addition of 5 mM glycine, (iv) standard medium without serine (0.4 mM glycine and 0 mM serine), (v) standard medium without serine and with addition of 2 mM glycine, and (vi) standard medium without serine and with addition of 5 mM glycine. Cell growth was measured in an incubator containing 5% $CO_2$ at 37° C. It was observed that, in the absence of exogenous serine, glycine inhibits transformed cell growth.

Example 2

Glycine Addition does not Further Deplete Cellular Serine Levels.

HEK293T cells were cultured for 24 h at 37° C. and 5% $CO_2$ in four different media conditions: (i) standard DMEM, (ii) DMEM+5 mM glycine, (iii) DMEM without serine, and (iv) DMEM without serine+5 mM glycine. Metabolites were then harvested by quickly aspirating media, washing with PBS buffer, and immediately adding −80° C. 80:20 methanol:water extraction solution at −80° C. Following quenching, the tissue culture dish was incubated at −80° C. for 15 min, and then the cells were scraped from the plate. After centrifuging the cell suspension at 5300×g for 10 min, the supernatant was kept and the debris was re-extracted with −80° C. 80:20 methanol:water. The resulting suspension was centrifuged again and the supernatant was combined with first supernatant. The samples were analyzed by LC-high-resolution full-scan electrospray ionization MS as described previously (Lu, W., Clasquin, M. F., Melamud, E., Amador-Noguez, D., Caudy, A. A., Rabinowitz, J. D., Metabolomic analysis via reversed-phase ion-pairing liquid chromatography coupled to a stand alone orbitrap mass spectrometer. *Anal. Chem.,* 82: 3212-3221 (2010)). LC separation was by reversed-phase ion-pairing chromatography with tributylamine as the ion-pairing agent. MS analysis was on a stand-alone orbitrap mass analyzer (Thermo Scientific) operated in negative ion mode and scanning from m/z 85-1000 at 1 Hz at 100,000 resolution. Data were analyzed using the MAVEN software suite. All observed LC-MS peaks were in analyzed, including those of roughly 100 known water-soluble metabolites.

Analysis of metabolite concentrations revealed that addition of glycine enhanced, rather than decreased, intracellular serine levels.

Example 3

Glycine Addition Depletes Cellular NADPH.

HEK293T cells were cultured in the conditions described in Example 2. In addition to measuring metabolite concentrations, important metabolite ratios, e.g., NADH/NAD+, NADPH/NADP+, ATP/ADP, were calculated. It was observed that removal of extracellular serine decreased the NADPH/NADP+ ratio. Moreover, it was observed that addition of glycine resulted in an approximately 2-fold decrease in the NADPH/NADP+ ratio, and also significantly decreased the ATP/ADP ratio. Thus, especially when serine is limiting, addition of glycine perturbs cellular redox balance, decreasing reducing power available for biosynthesis and antioxidant defense.

Example 4

Serine not Glycine Contributes the One-Carbon Unit Pool

Previous studies (Zhang et al., Cell 148:259-272, 2012) have suggested that glycine is a source of one carbon units. Other prominent work pointed to glycine as a proliferation-linked nutrient for cancer cell proliferation (Jain et al., Science 336(6084):1040-4, 2012). Experiments were undertaken herein to determine whether glycine or serine contributes a single carbon in the cellular environment. One-carbon metabolism is described in Amelio et al., Trends Biochem Sci. 2014; 39(4): 191-198. 2014.

In order to determine contribution of the single carbon, cells were cultured with media containing [U $^{13}$C] serine for 48 h, washed three times with cold PBS to remove extracellular serine, extracted, and the intracellular labeling pattern analyzed by LC-MS for ATP (representing purines; there is no labeling of ribose-phosphate based on LC-MS measurements), glycine and serine. See e.g., Fan et al., Nature 510: 298-302, 2014.

Figure 1:
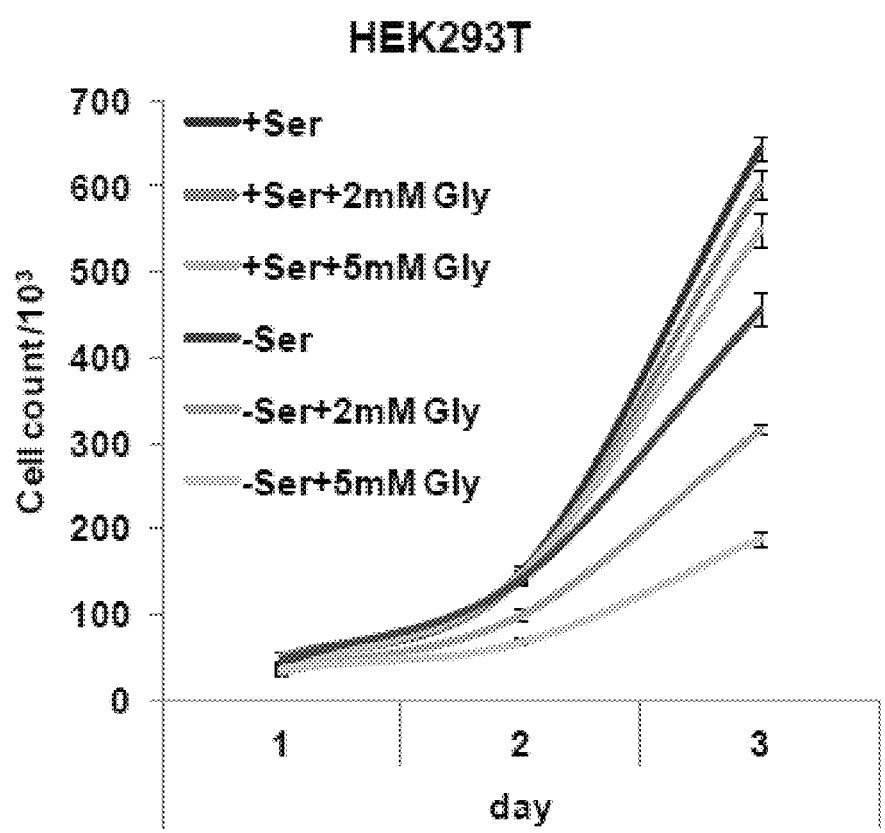
Figure 2A:
FIGS. 2A-2H show glycine addition does not further deplete cellular serine levels.
Figure 2B:
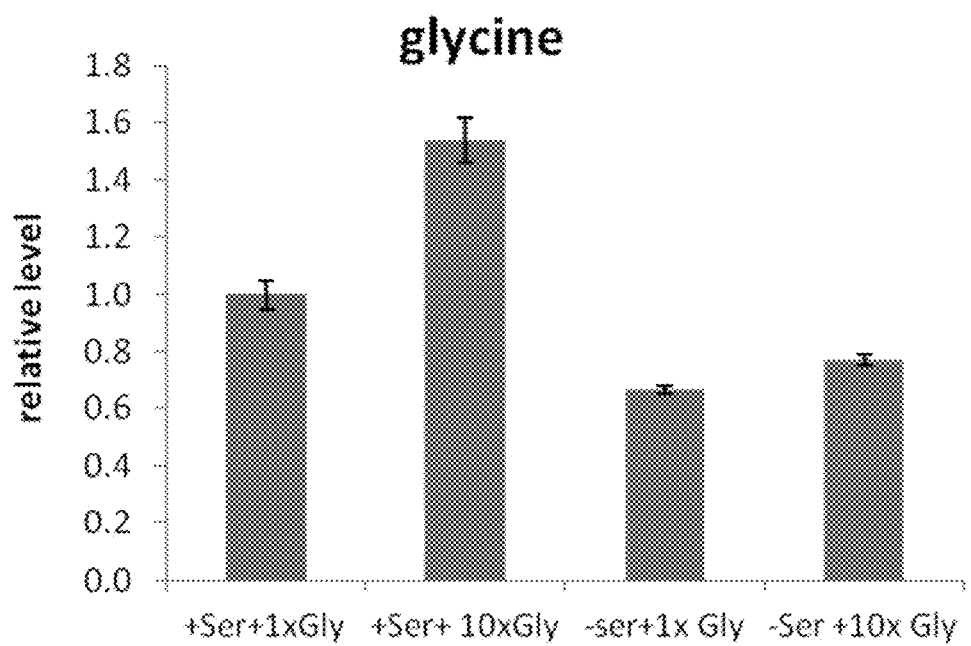
Figure 2C:
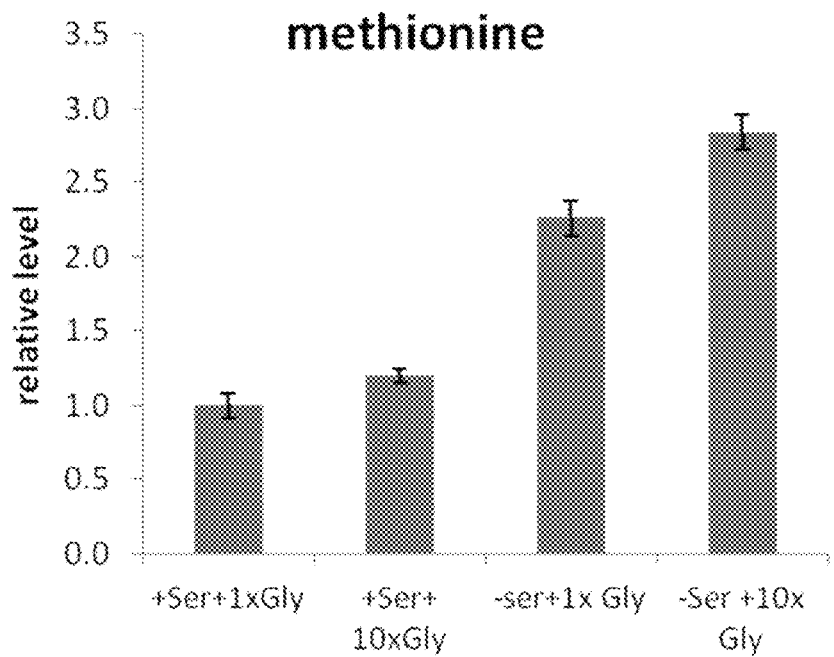
Figure 2D:
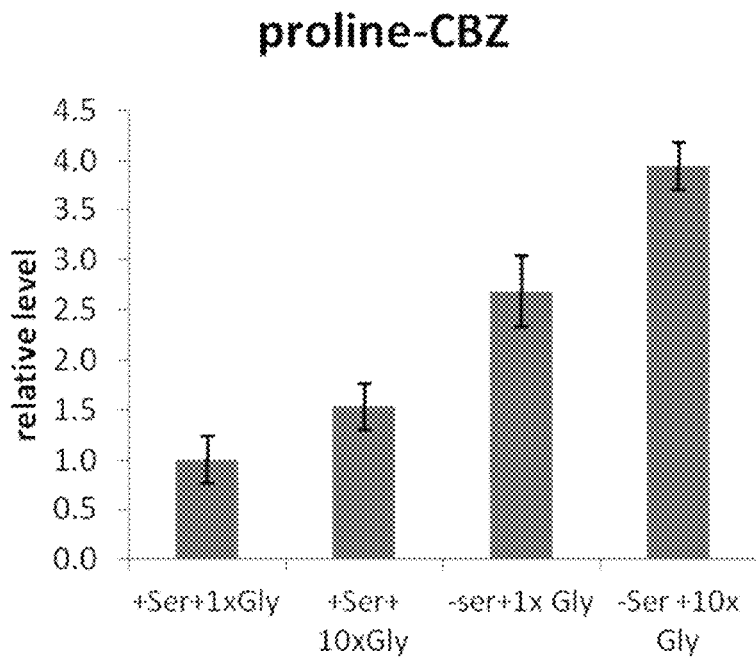
Figure 2E:
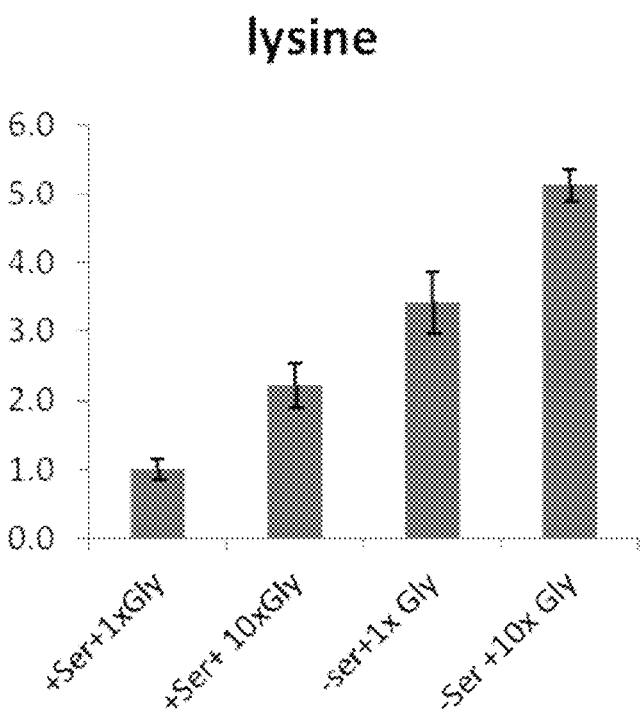
Figure 2F:
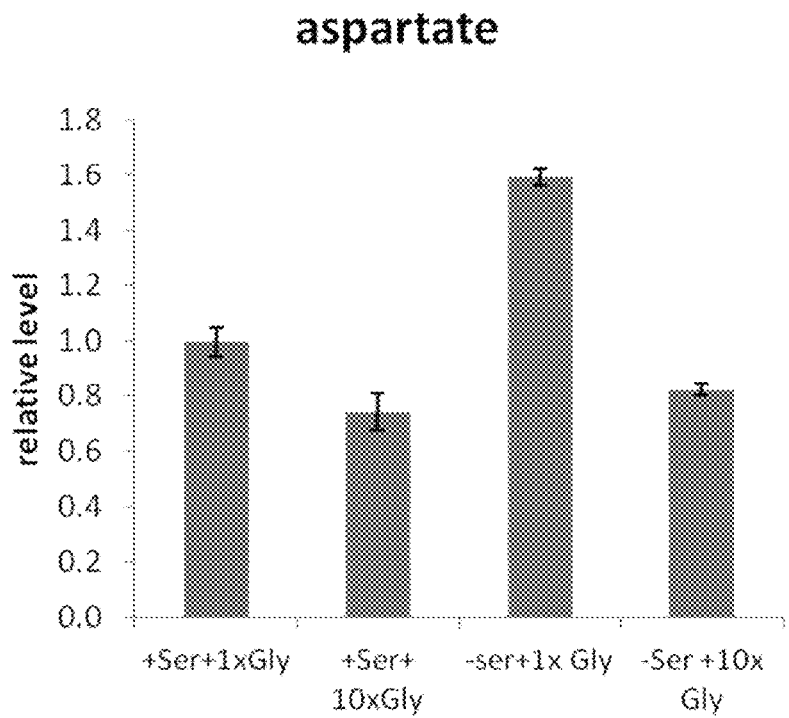
Figure 2G:
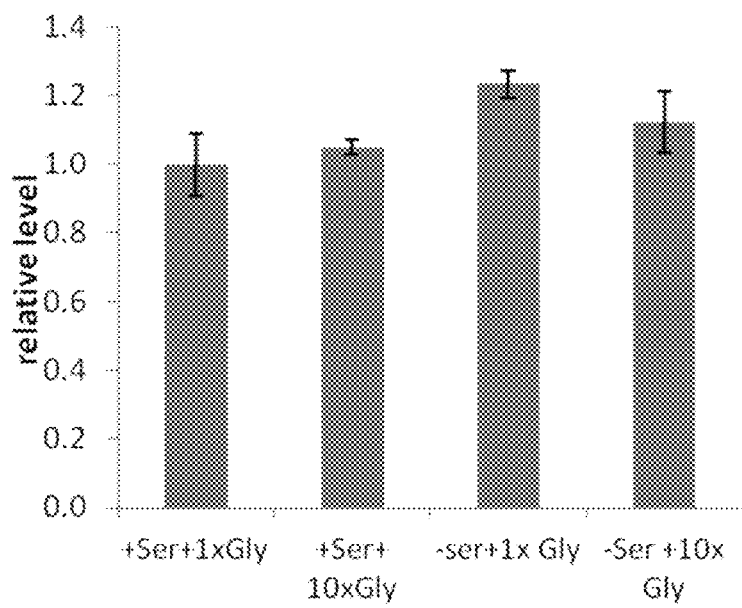
Figure 2H:
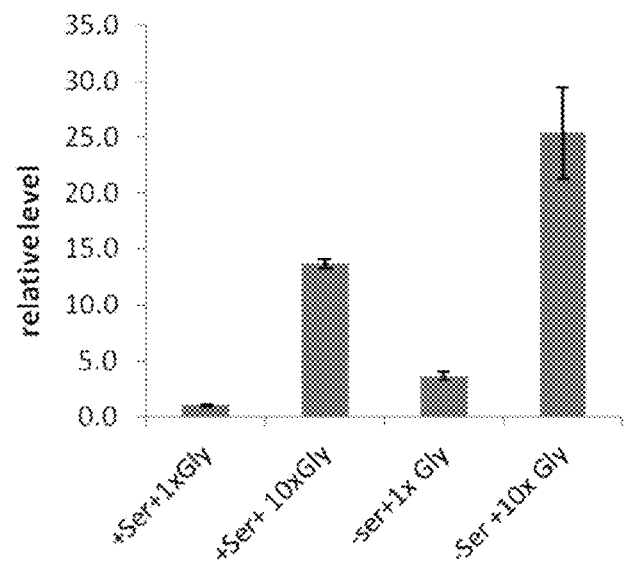
Figure 3A:
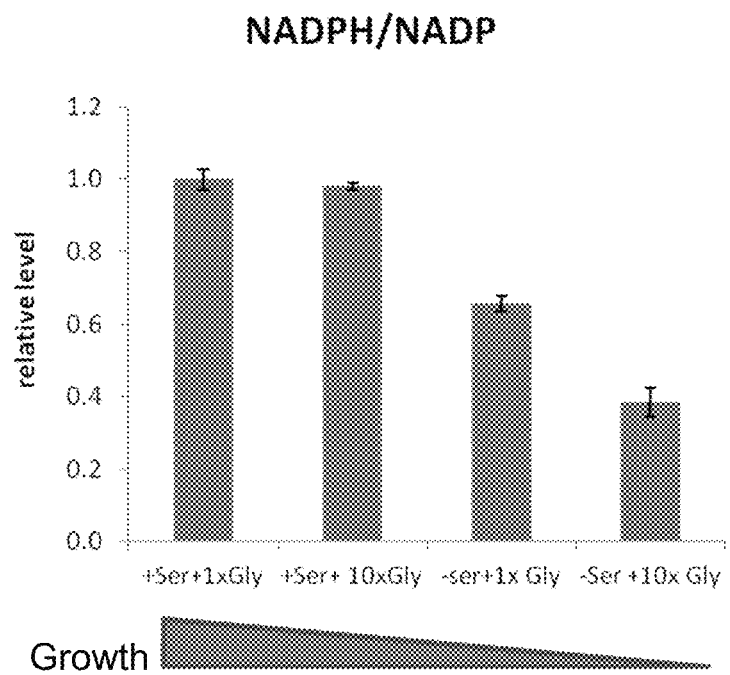
FIGS. 3A-3B show glycine addition depletes cellular NADPH.
Figure 3B:
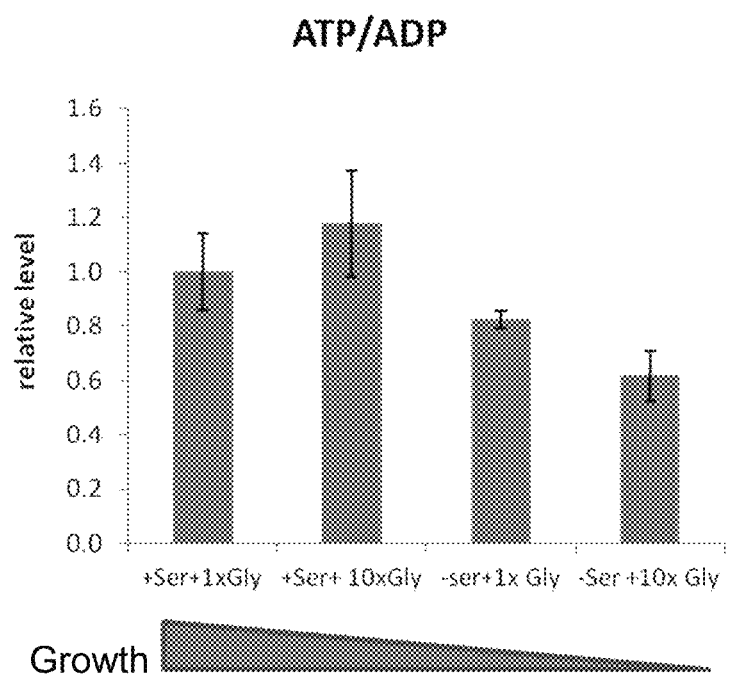
Figure 4A:
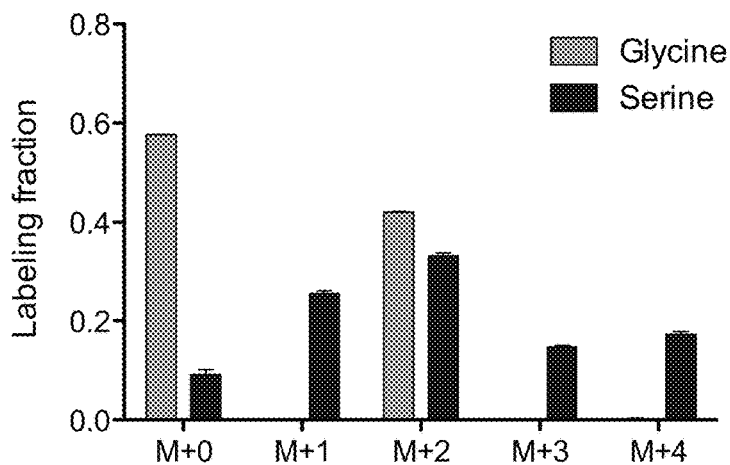
FIGS. 4A-4C show (FIG. 4A) ADP labeling from U13C tracer. U13C-serine but not U13C-glycine contributes one carbon units into the ADP purine ring in cultured HEK293T cells.
Figure 4B:
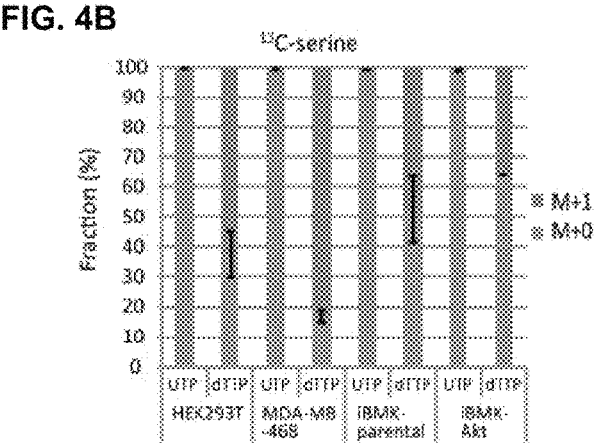
Figure 4C:
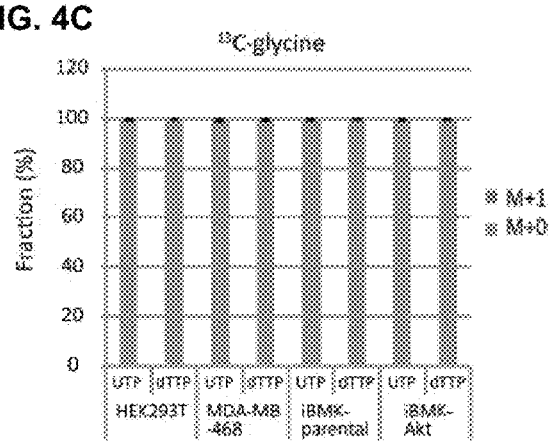

Experimental results show that serine but not glycine contributes to the cellular one-carbon unit pool. FIG. 4A shows that $U^{13}C$-serine but not $U^{13}C$-glycine contributes one carbon units into the ADP purine ring in cultured HEK293T cells (results also validated in MDA-MB-468 cells and immortalized baby mouse kidney cells). Purine ring labeling is indicative of formyl-THF labeling. Glycine is directly incorporated into the purine ring, explaining the $M^{+2}$ labeling of the purine ring from $U^{13}C$-glycine, despite glycine not contributing any one carbon units. FIG. 4B shows that $U^{13}C$-serine labels the methyl group that differentiates dTTP from UTP, indicative of methylene-THF labeling while FIG. 4C shows that $U^{13}C$-glycine does not label the methyl group of dTTP, and thus does not label methylene-THF. These results show that glycine does not contribute one carbon units and lays the groundwork for glycine acting as an anticancer agent and not a pro-cancer agent. The experiments in Maddocks et al. (Nature 2013) focused on the fact that low serine inhibits tumor growth, but the treatment was actually removal of both serine and glycine—the fact that low serine+high glycine further impairs growth is novel. Thus, the anti-proliferative/anti-cancer activity of glycine observed herein was surprising and unexpected.

Example 5

AICAR as an Indicator of Formyl-THF Deficiency

The following experiments establish the metabolic intermediate AICAR (purine biosynthetic intermediate 5-aminoimidazole-4-carboxamide ribotide) as an indicator of formyl-THF deficiency. AICAR in wild type HEK293T cells and cells lacking a key enzyme producing formyl-THF, MTHFD2, was measured by LC-MS. See e.g., Fan et al., Nature 510: 298-302, 2014. The LC-MS extracted ion chromatogram (chromatogram limited to compounds with the exact mass of AICAR) shows that wild type cells have low AICAR while ΔMTHFD2 cells have high AICAR. The ΔMTHFD2 cells lacking MTHFD2 were produced from HEK293T cells by CRISPR (clustered regularly interspaced short palindromic repeat)-mediated knockout. FIG. 5 shows that addition of formate, which is assimilated to form formyl-THF, rectifies the formyl-THF status and thus eliminates the AICAR accumulation.

Knockout of additional enzymes (MTHFD1, MTHFD2, SHMT, SHMT2, MTHFD1L, ALDH1L1, ALDH1L2) by CRISPR in HEK293T cells was carried out. Knockout of all of the enzymes is complete, with the exception of MTHFD1, where only one copy of the gene is lost, because the enzyme is essential. The cells deficient in MTHFD1, SHMT2, MTHFD2, and MTHFD1L accumulate AICAR to >50-fold normal levels. The other cell lines have normal AICAR. These results establish a pathway of one carbon flux from serine in the mitochondrion, via SHMT, to mitochondrial methylene-THF, via MTHFD2 into mitochondrial formyl-THF, and then via MTHFD1L into free formate which crosses into the cytosol and is converted by MTHFD1L into cytosolic formyl-THF. These results further validate AICAR as an indicator of formyl-THF deficiency.

Example 6

Glycine Addition Depletes Cellular 1C-Loaded Folates

Folate measurement by LC-MS is employed to generate data showing directly that glycine addition depletes cellular 1C-loaded folates (formyl-THF and 5-methyl-THF). THF species exist in multiple polyglutamate forms in cell culture. To measure cellular folates, media was removed from HEK293T cells, and replaced with 50:50 methanol:water with 25 mM ammonium acetate and 1% sodium ascorbate, at −20° C. Ascorbate acts as an antioxidant in the media to protect THF species from oxidative loss. After 15 min on ice, the cells were scraped from the dish to further enhance extraction, and the cell-liquid mixture was centrifuged to remove particulate matter. The particulate matter was re-extracted with the same solvent for 15 minutes, and the 2 extracts were combined. The resulting combined extract was treated with rat serum to hydrolyze the polyglutamate chains of folate polyglutamates. Rat serum contains glutamate hydrolase to remove polyglutamate chains and increases signal by condensing the polyglutamate THF species to monoglutamate THF. The resulting mixture was passed through a phenyl solid phase extraction column which removes proteins, highly soluble metabolites, salts and further concentrates the folate species, which were then analyzed by in high resolution LC-MS.

FIG. 6 shows the impact of media serine and glycine on formyl-THF and methyl-THF levels measured in media containing serine and glycine at the levels indicated. The concentrations of 1× and 10× are relative to standard DMEM (Dulbecco's Modified Eagle Medium). The Y-axis for the formyl-THF and AICAR is log scale. Formyl-THF and methyl-THF levels decrease in the presence of glycine when serine is absent. The rise in AICAR with glycine addition (FIG. 6C) further proves the functional one-carbon unit depletion by the amino acid.

FIG. 7A shows a diagram of the hypothetical manner in which glycine is acting. It is hypothesized that high glycine is driving the backwards SHMT reaction while also impairing the forward reaction by product inhibition. Analysis of the relative HEK293 cell number after culture for 3 days shows that cell growth (relative to growth in complete DMEM) is decreased in DMEM lacking serine but containing 1× glycine such that the final cell number is lower by approximately 30%, Simultaneous serine removal and addition of 12× results in a decrease in final cell number of approximately 70%. Relative NADPH/NADP+ was also measured in HEK293 cells after 3 days culture and shown to decrease in DMEM lacking serine but having 1× glycine from approximately 1 to approximately 0.7, and decrease further when cultured in DMEM lacking serine with addition of 12× glycine (to approximately 0.45). FIGS. 7B and 7C show labeling of serine and glycine after feeding with $U^{13}C$ serine or $U^{13}C$ glycine and reveals reverse serine hydroxymethyltransferase flux.

Example 7

Xenograft Growth in Mice Fed a Serine-Free High Glycine Diet

In order to determine the effects of administration of or consumption of high glycine in tumor progression of a subject, animal models are used.

Approximately $3 \times 10^6$ HCT116 cells (or other tumor-forming transformed cells) are injected on the flank of approximately 8 week CD-1-Foxn1nu female mice (Charles River) or similar rodents. To compare cell lines or gather data more rapidly, different cell lines can be ejected on the 2 flanks (right and left) of each mouse. Immediately following injection, mice are placed on one of 5 diets (or a subset thereof): (i) control diet (containing serine and glycine as part of the amino-acid mix), (ii) diet deficient in serine and glycine (which can be obtained from a vendor such as International Product Supplies), (iii) diet deficient in serine and containing normal glycine, (iv) diet deficient in serine and containing high (2×-5× normal) glycine, and (v) diet containing normal serine and high glycine. Numbers of mice are selected in order to obtain appropriate statistical power, with 6-20 mice per group typical.

Exemplary control diet ingredients are as described in Maddocks et al., 2013: sucrose (25.9%), corn starch (41.8%), corn oil (5.0%), Baker amino acid vitamin mix (0.2%), Baker amino acid mineral mix (10.0%), sodium bicarbonate (1.0%), dl-alpha tocopheryl acetate (0.004%), ethoxyquin (preservative, 0.019%), choline chloride (0.1%), amino acid premix (16.0%). Amino acid pre-mix: l-arginine-HCL (1.60%), l-cystine (0.64%), l-glutamine (1.60%), glycine (1.33%), l-histidine-HCL (0.80%), l-isoleucine (1.07%), l-leucine (1.60%), l-lysine-HCL (1.87%), l-methionine (0.80%), l-phenylalanine (1.07%), l-serine (1.33%), l-threonine (1.07%), l-tryptophan (0.27%), l-tyrosine (0.53%), l-valine (1.07%). For the experimental diets, the amino acid premix is modified to (ii) eliminate serine and glycine and increase correspondingly the fractions of the other amino acids, (iii) eliminate serine and increase correspondingly the fractions of the other amino acids, (iv) eliminate serine and increase glycine, modifying correspondingly the fractions of other amino acids, and (v) increase glycine, modifying correspondingly the fractions of other amino acids. To the extent feasible, diets comprise equal calorific value and equal total amino acid content. Animals are housed in sterile cages with tumor volumes monitored by imaging (e.g., ultrasound) optionally before during and after treatment with the glycine regimen and control diets. Efficacy of the treatments will be determined by comparison of tumor volumes between treatment groups, as well as analyzing overall mouse survival until death, tumor ulceration, or until tumor volume surpasses a predetermined volume. Upon reaching the endpoint of the study, mice will be humanely killed, tumors isolated, and metabolic contents and other biological properties monitored using methods such as LC-MS and histopathology. Based on the findings herein, it is expected that glycine treatment will reduce tumor growth and slow tumor progression in subjects receiving high glycine therapy.

Example 8

Clinical Trial of Glycine Supplementation

Patients presenting with the targeted disease state (e.g., metastatic breast cancer, lung cancer, Crohn's disease, or otherwise from those specified above) are offered the opportunity to participate in a clinical trial consisting of current best therapy (e.g., for stage IV lung cancer, cytotoxic combination chemotherapy with cisplatin and pemetrexed) with or without glycine supplementation therapy. The trial may be designed so as to offer only a specific standard of care therapy regimen, or so as to allow a physician to select the most appropriate therapy for the patient. Individuals providing informed consent to enter the trial are randomized to the current best therapy or current best therapy plus glycine supplementation therapy arms. For a clinical trial, the typical number of patients per group ranges from 8-800 depending on the disease state and trial phase (e.g., Phase III trials require greater numbers of patients than Phase II trials).

The glycine supplementation therapy arm involves providing increased total intake of glycine and/or decreased total intake of serine so as to achieve an increased ratio of glycine to serine intake. The clinical course of patients enrolled in the trial is monitored with respect to endpoints selected based on the disease state, e.g., for stage IV lung cancer, changes in tumor volume, progression-free survival, and overall survival, as well as side effects of the treatment regimen. Efficacy of the glycine supplementation therapy is determined by comparison of outcomes between the treatment groups. Based on the findings herein, it is expected that glycine treatment will reduce tumor growth and slow tumor progression in subjects receiving high glycine therapy.

Numerous modifications and variations to the present disclosure, as set forth in the embodiments and illustrative examples described herein, will be apparent to persons of ordinary skill in the art. All such modifications and variations are intended to be within the scope of the present disclosure and the appended claims.

REFERENCES

Maddocks O D K, Berkers C R, Mason S M, Zheng L, Blyth K, Gottleib E, Vousden K. Serine starvation induces stress and P53-dependent metabolic remodelling in cancer cells. Nature, 2013, 493, 542-549

Kamphorst J J, Cross J R, Fan J, de Stanchina E, Mathew R, White E P, Thompson C B, Rabinowitz J D. Hypoxia and Ras-transformed cells support growth by scavenging unsaturated fatty acids from lysophospholipids. PNAS, 2013, 110, 8882-8887

Poirson-Bichat F, Bras Goncalves R A, Miccoli L, Dutrillaux B, Poupon M F. Methionine depletion enhances the antitumoral efficacy of cytotoxic agents in drug-resistant human tumor xenografts. Clinical Cancer Research, 2000, 6, 643-653.

Cao W X, Ou J M, Fei X F, Zhu Z G, Yin H R, Yan M, Lin Y Z. Methionine-dependence and combination chemotherapy on human gastric cancer cells in vitro. World Journal of Gastroenterology, 2002, 8, 230-232

Khan O, La Thangue N B. HDAC inhibitors in cancer biology: emerging mechanisms and clinical applications. Immunol Cell Biol, 2012, 90, 85-94

Funahashi H, Satake M, Hasan S, Sawai H, Newman R A, Reber H A, Hines O J, Eibl G. Opposing effects of n-6 and n-3 polyunsaturated fatty acids on pancreatic cancer growth. Pancreas. 2008, 36, 353-362.

Bradley M C, Hughes C M, Cantwell M M, Napolitano G, Murray L J. Non-steroidal anti-inflammatory drugs and pancreatic cancer risk: a nested case-control study. British Journal of Cancer, 2010, 102, 1415-1421.

Zhang et al., Glycine Decarboxylase Activity Drives Non-Small Cell Lung Cancer Tumor-Initiating Cells and Tumorigenesis. Cell 148:259-272, 2012.

Jain et al., Metabolite profiling identifies a key role for glycine in rapid cancer cell proliferation. Science 336 (6084):1040-4, 2012.

Amelio et al., Serine and glycine metabolism in cancer. Trends Biochem Sci. 2014; 39(4): 191-198. 2014.

What is claimed:

1. A nutritional supplement comprising an amino acid consisting of serine and glycine, wherein serine and glycine are present at a molar ratio of serine to glycine of about 3:1 to about 100:1.

2. The nutritional supplement of claim 1 wherein the molar ratio of serine to glycine is about 3:1, 4:1, 5:1, 6:1, 7:1, 8:1, 9:1, 10:1, 20:1, 30:1, 40:1, 50:1, 60:1, 70:1, 80:1, 90:1, or 100:1.

3. A method of alleviating cancer comprising administering to a subject in need thereof a diet comprising the nutritional supplement of claim 1.

4. A method of alleviating cancer comprising administering to a subject in need thereof one or more pharmacological inhibitors of cancer cell growth and instructing the subject to consume a diet comprising the nutritional supplement of claim 1.

5. The method of claim 4, wherein the subject is further instructed to reduce consumption of serine, methionine, choline, or a combination thereof.

6. The method of claim 4, wherein the subject is additionally instructed to consume a supplement comprising homocysteine.

7. The method of claim 4, wherein the pharmacological inhibitor is an inhibitor of folate metabolism or is an inhibitor of DNA methylation.

8. A pharmaceutical composition comprising an amino acid consisting of serine and glycine, and a pharmaceutically acceptable carrier, wherein serine and glycine are present at a molar ratio of serine to glycine of about 3:1 to about 100:1.

9. The nutritional supplement of claim 1, further comprising homocysteine.

10. The nutritional supplement of claim 1, further comprising an inhibitor of DNA methylation.

11. The pharmaceutical composition of claim 8, wherein the molar ratio of serine to glycine is about 3:1, 4:1, 5:1, 6:1, 7:1, 8:1, 9:1, 10:1, 20:1, 30:1, 40:1, 50:1, 60:1, 70:1, 80:1, 90:1, or 100:1.

12. The pharmaceutical composition of claim 8, further comprising homocysteine.

13. The pharmaceutical composition of claim 8, further comprising an inhibitor of DNA methylation.

* * * * *